United States Patent [19]

McLaughlin et al.

[11] Patent Number: 5,273,056
[45] Date of Patent: Dec. 28, 1993

[54] USE OF COMBINATIONS OF VISCOELASTICS DURING SURGERY

[75] Inventors: Richard N. McLaughlin, Arlington; Ole J. Lorenzetti, Fort Worth, both of Tex.

[73] Assignee: Alcon Laboratories, Inc., Fort Worth, Tex.

[21] Appl. No.: 897,733

[22] Filed: Jun. 12, 1992

[51] Int. Cl.$^5$ .............................................. A61B 19/00
[52] U.S. Cl. ................................... 128/898; 606/107; 604/294
[58] Field of Search ......................... 128/897–899; 606/107; 604/289, 294–300, 28; 351/167, 177; 424/427, 429

[56] References Cited

U.S. PATENT DOCUMENTS

| | | | |
|---|---|---|---|
| 4,141,973 | 2/1979 | Balazs | 424/180 |
| 4,328,803 | 5/1982 | Pape | 128/276 |
| 4,340,037 | 7/1982 | Lewicky | 604/28 |
| 4,486,416 | 12/1984 | Soll et al. | 424/180 |
| 4,965,253 | 10/1990 | Goldberg et al. | 604/28 |
| 5,103,840 | 4/1992 | Kavoussi | 128/879 |

OTHER PUBLICATIONS

Olson, Randall J., "A Brief Review of Viscoelastics," Clinical Research Forum, Mar. 15, 1990, p. 19.
Glasser et al., "A Comparison of the Efficacy and Toxicity of and Intraocular Pressure Response to Viscous Solutions in the Anterior Chamber," Arch. Ophthalmol. (104), Dec. 1986, pp. 1819-1824.
Glasser et al., "Endothelial Protection and Viscoelastic Retention During Phacoemulsification and Intraocular Lens Implantation," Arch. Ophthalmol. (109), Oct. 1991, pp. 1438-1440.
"The Healon ® Difference"-Kabi Pharmacia.
Healon ®-Product Insert.
Healon ® G.V.-Product Insert.
Orcolon ®-Product Insert.
Orcolon ®-Product Information Brochure.
"Protect the cells you can never replace"-Weck, Sep. 1989.
Vitrax TM -Product Insert.
"For Surgeons Interested in Today's Advanced Surgical Techniques"-Storz Ophthalmics, Inc., Sep. 1991.
Occucoat ®-Product Information.
Amvisc ® Plus-Product Information.
Amvisc ®-Product Information.
"What Makes Viscoat ® Different Before Surgery'"-Alcon Surgical, Inc.
Viscoat ®-Product Information.
"Central Core Viscectomy to Remove Viscoat ®"-Alcon Surgical, Inc.
Viscoat ®-Product Monograph.

*Primary Examiner*—Lee S. Cohen
*Assistant Examiner*—John A. Lacyk
*Attorney, Agent, or Firm*—James A. Arno; Sally S. Yeager; Barry L. Copeland

[57] ABSTRACT

A method for conducting ocular surgery using different viscoelastic agents is disclosed.

9 Claims, No Drawings

USE OF COMBINATIONS OF VISCOELASTICS DURING SURGERY

The present invention is directed towards the use of different viscoelastic agents during a single surgical procedure. In particular, the use of two viscoelastic agents in ophthalmic surgery, such as cataract surgery, is described.

BACKGROUND OF THE INVENTION

There are known viscous or viscoelastic agents for ophthalmic surgical use, for example, Viscoat ® (Alcon Surgical, Inc.) which contains the viscoelastics, sodium hyaluronate and chondroitin sulfate; Healon ® and Healon GV (Kabi Pharmacia), Amvisc Regular and Amvisc Plus (IOLAB), and Vitrax (Allergan) which contain sodium hyaluronate; Orcolon (Optical Radiation Corporation) which contains a polyacrylamide; and Occucoat (Storz) which contains hydroxypropylmethylcellulose (HPMC). All of these products are useful in cataract surgery. They are used by the skilled ophthalmic surgeon for several purposes: maintenance of the anterior chamber of the eye and protection of ophthalmic tissues during surgery, particularly corneal endothelial cells, and as an aid in manipulating ophthalmic tissues.

While all of the products described above may be used during cataract surgery, there is no one product, or viscous or viscoelastic agent (hereinafter "agent") which best fulfills all of the purposes. All have their own advantages and disadvantages. For example, Viscoat ® works extremely well in maintaining the anterior chamber during capsulotomoy, or anytime during the cataract procedure, and in adhering to and protecting tissues, particularly the corneal endothelium. But, Viscoat ®, due to its adhering and coating characteristics is relatively difficult to remove from the anterior chamber of the eye. In addition, although it can be used to manipulate tissue for insertion of an intraocular lens into the eye, other agents are known to work better for this purpose.

Pure sodium hyaluronate products can be very useful in manipulating tissues during surgery, for example, they can be used to inflate the capsular bag to facilitate the insertion of an intraocular lens (IOL). However, sodium hyaluronate is not as effective as some agents in maintaining the anterior chamber and protecting ophthalmic tissues. Because it is highly cohesive, and thus very useful in manipulation, it is not as effective in adhering to, and protecting tissues. Its cohesiveness also makes it easier to remove from the eye at the end of surgery.

HPMC adheres well to ophthalmic tissues and therefore protects them, but is not as good as, for example, Viscoat ®, in maintaining the anterior chamber, or as good as sodium hyaluronate in manipulating tissues. However, it can be easily diluted with irrigation fluid following IOL implantation. This helps prevent intraocular pressure spikes following surgery.

In general, products containing relatively higher molecular weights of sodium hyaluronate are more effective in maintaining the anterior chamber and protecting tissues than relatively lower molecular weight sodium hyaluronate products; however, they tend to be highly cohesive and may be prematurely aspirated from a surgical site. Products, which due to their tenacious characteristics adhere to and protect tissues, are more difficult to remove from the surgical site.

It would be advantageous to use more than one agent during an ophthalmic procedure, such as a cataract operation, to obtain the maximum benefits offered by the variety of available viscoelastic agents. The methods of the present invention provide this advantage.

SUMMARY OF THE INVENTION

The present invention is directed to the use of more than one agent during surgery, particularly ophthalmic surgery. The method is employed during ophthalmic surgery in order to best maintain the anterior chamber, protect the tissues of the eye, and provide for manipulation of ophthalmic tissues.

DESCRIPTION OF THE PREFERRED EMBODIMENT

The method of the present invention is directed to the use of more than one viscoelastic agent during cataract surgery as performed by a skilled ophthalmic surgeon. One agent is used during capsulotomy and irrigation/aspiration or phacoemulsification of the cataractous lens (Stage 1) and a different agent is used following extraction of the lens and during implantation of an intraocular lens (Stage 2).

The agent used during Stage 1 of the surgery should be adherent enough to be retained in the anterior chamber, that is, it should effectively maintain anterior chamber space and also relieve lens convexity, i.e., flatten the lens somewhat so that a capsulotomy can be done with more control and less chance of peripheral capsular tearing. The agent should also protect the tissues, particularly the corneal endothelial cells, from trauma resulting from shear forces and direct contact from nuclear fragments and instruments. The agent used during Stage 2 should effectively allow for implantation of an IOL by being used to manipulate tissue, i.e., filling and opening the capsular bag which is where the IOL will be placed, and also maintaining the anterior chamber prior to and during implantation of the IOL.

For Stage 1 of a cataract procedure it is appropriate to employ an agent that has characteristics that will enable it to function as previously discussed, i.e., it will maintain the anterior chamber and protect the ophthalmic tissues from trauma during capsulotomy and removal of the cataract. The agent to be used during Stage 2 should have characteristics that allow it to be used as a tool for manipulating tissue, i.e., inflation of the capsular bag and insertion of an IOL within the bag. It should also be relatively easy to remove from the eye after IOL implantation.

Viscoelastic agents which are useful for methods of the present invention include but are not limited to: sodium hyaluronate, chondroitin sulfate, polyacrylamide, HPMC, proteoglycans, collagen, methylcellulose, carboxymethyl cellulose, ethylcellulose, and keratin of various molecular weights, or combinations thereof. Whether it is appropriate to use an agent for Stage 1 or Stage 2 of a cataract procedure will depend on the physical and chemical characteristics of each agent or combination, including, but not limited to, their molecular weight, viscosity, pseudoplasticity, elasticity, rigidity, coatability, cohesiveness, and molecular charge, and the agent's concentration in a product.

The preferred method involves the use of an agent containing sodium hyaluronate and chondroitin sulfate, such as Viscoat ®, during Stage 1 of the procedure and a relatively high molecular weight sodium hyaluronate product, such as Provisc ® or Healon ® during Stage 2. More particularly, Viscoat® is used upon the surgeon's entrance into the anterior chamber mainly to fill and maintain the chamber and protect the tissues during capsulotomy and phacoemulsification and or irrigation/aspiration and removal of the cataractous lens elements. A high molecular weight sodium hyaluronate product, such as Provisc® or Healon® is then introduced as a viscoirrigant replacing the Viscoat® or after removal of some or all of the Viscoat®. It can also be used to maintain the anterior chamber but is introduced into the empty capsular bag to inflate it for introduction and placement of an IOL. Upon completion of IOL placement the sodium hyaluronate can be removed to help prevent a post surgical sharp increase in intraocular pressure. The use of these two agents during cataract surgery provides for optimal maintenance of the anterior chamber, protection of tissues, and manipulation of the capsular bag for IOL implantation.

More than one agent can be employed by the skilled surgeon in a variety of procedures by choosing an agent with the desired characteristics to either help manipulate tissues or function as an adhesive, protective agent. For example, a vitrectomy may require much tissue manipulation and therefore, a pure sodium hyaluronate product would be most useful as an aid to such manipulation. If the procedure involves a detached retina, use of a product with good adhesive properties, like Viscoat®, can be employed prior to closing to serve as a tamponade.

We claim:

1. A method for conducting ocular surgery in a human eye having an anterior chamber, a posterior chamber and a capsular bag located within the posterior chamber, comprising:
   surgically opening the eye;
   filling the anterior chamber with a first viscoelastic agent;
   performing a capsulotomy;
   removing any cataractous tissue;
   filling the capsular bag with a second viscoelastic agent; and
   implanting an intraocular lens in the capsular bag.

2. The method of claim 1 which further comprises removing the first viscoelastic agent prior to filling the capsular bag with the second viscoelastic agent.

3. The method of claim 1 which further comprises removing the second viscoelastic agent after intraocular lens is in the capsular bag.

4. The method of claim 1 wherein the first viscoelastic agent comprises a mixture of sodium hyaluronate and chondroitin sulfate.

5. The method of claim 1 wherein the second viscoelastic agent comprises sodium hyaluronate.

6. A method for conducting cataract surgery in a human eye having an anterior chamber, a posterior chamber and a capsular bag located within the posterior chamber, comprising:
   surgically opening the eye;
   filling the anterior chamber with a mixture of sodium hyaluronate and chondroitin sulfate;
   performing a capsulotomy;
   removing any cataractous tissue;
   filling the capsular bag with sodium hyaluronate; and
   implanting an intraocular lens in the capsular bag.

7. A method for conducting an ocular surgical procedure comprising:
   surgically opening the eye;
   performing an ocular surgical procedure at a surgical site; and
   during said ocular surgical procedure sequentially introducing to said surgical site multiple viscous or viscoelastic agents wherein such agents exhibit differing cohesive or adherent properties.

8. The method of claim 7, wherein a first agent exhibits relatively greater adherent properties and a second agent exhibits relatively greater cohesive properties.

9. The method of claim 8, wherein the surgical procedure is cataract surgery.

* * * * *

(12) EX PARTE REEXAMINATION CERTIFICATE (4968th)
United States Patent
McLaughlin et al.

(10) Number: US 5,273,056 C1
(45) Certificate Issued: Jul. 27, 2004

(54) USE OF COMBINATIONS OF VISCOELASTICS DURING SURGERY

(75) Inventors: Richard N. McLaughlin, Arlington, TX (US); Ole J. Loreazetti, Fort Worth, TX (US)

(73) Assignee: Alcon Manufacturing, Ltd., Fort Worth, TX (US)

Reexamination Request:
No. 90/006,400, Oct. 8, 2002

Reexamination Certificate for:
Patent No.: 5,273,056
Issued: Dec. 28, 1993
Appl. No.: 07/897,733
Filed: Jun. 12, 1992

(51) Int. Cl.[7] .............................................. A61B 19/00
(52) U.S. Cl. ...................... 128/898; 606/107; 604/294
(58) Field of Search ........................ 128/898; 424/78.04

(56) References Cited

U.S. PATENT DOCUMENTS 4,908,015 A * 3/1990 Anis ........................... 604/22

OTHER PUBLICATIONS

Olson, Randall J., Dr., *A Brief Review of Viscoelastics*, Clinical Research Forum, (Mar. 15, 1990).
Glasser et al., *A Comparison of the Efficacy and Toxicity of and Intraocular Pressure Response to Viscous Solutions in the Anterior Chamber*, Laboratory Sciences, Arch Ophthalmol–vol. 104, (Dec. 1986).
Glasser et al., *Endothelial Protection and Viscoelastic Retention During Phacoemulsification and Intraocular Lens Implantation*, Laboratory Sciences, Arch Ophthalmol–vol. 109, (Oct. 1991).
Apple, D.J., M.D., *Comparison of endothelial cell loss 2 months after in–situ phacoemulsification, The Healon® Difference,* Kabi Pharmacia Ophthalmics Inc.
Healon® Instructions.
Healon® G.V. Instructions Mode D'Emploi, Pharacia.
Brochure for Orcolon®, *The Ideal Viscoelastic Designed for Today's Phaco Surgeon,* ORC, *Progess in Ophthalmology series,* vol. 11 (1990).
Brochure for Orcolon® Product Information, Optical Radiation Corporation (Dec. 1988).
Brochure for Vitrax(sodium hyaluronate), *Protect the cells you can never replace,* WECK (Sep. 1989).
Brochure for Vitrax Product Information, WECK (Feb. 1989).
Brochure "For Surgeons Interested in Today's Advanced Surgical Techniques" Storz Ophthalmics, Inc. (1991).
Brochure for Product Information on OCCUCOAT, Storz.
Brochure for AMVISC® PLUS Product Information, MedChem Products, Inc.(1988).
Brochure for AMVISC® Product Information, MedChem Products, Inc. (1988).
Brochure for VISCOAT®, Alcon Surgical, Inc. (1989).
Brochure for VISCOAT®, Alcon Surgical, Inc. (1989).
Anderson, C.J., M.D. *Removing VISCOAT® After Lens Implanatation,* Alcon Surgical (no date).
*Viscoat™ Sodium Chondroitin Sulfate–Sodium Hyaluronate,* Cilco®, Inc., Huntington, WV (Mar. 1984).
Liesegang, Thomas J., M.D., *Viscoelastic Substances in Ophthalmology,* Survey of Ophthalmology, vol. 34, No. 4 (Jan./Feb. 1990).

* cited by examiner

Primary Examiner—Corrine McDermott

(57) ABSTRACT

A method for conducting ocular surgery using different viscoelastic agents is disclosed.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–9 is confirmed.

* * * * *